(12) United States Patent
Fujiu et al.

(10) Patent No.: US 11,412,978 B2
(45) Date of Patent: Aug. 16, 2022

(54) INFORMATION PROCESSING SYSTEM AND PROGRAM

(71) Applicants: THE UNIVERSITY OF TOKYO, Tokyo (JP); SIMPLEX QUANTUM Inc., Tokyo (JP)

(72) Inventors: Katsuhito Fujiu, Tokyo (JP); Issei Komuro, Tokyo (JP); Eriko Hasumi, Tokyo (JP); Yu Shimizu, Tokyo (JP); Yoshihiro Mikami, Tokyo (JP); Ryu Saito, Tokyo (JP); Minoru Shiratsuchi, Tokyo (JP); Ying Chen, Tokyo (JP); Yuji Hamada, Tokyo (JP)

(73) Assignees: THE UNIVERSITY OF TOKYO; SIMPLEX QUANTUM INC.

( * ) Notice: Subject to any disclaimer, the term of this patent is extended or adjusted under 35 U.S.C. 154(b) by 0 days.

(21) Appl. No.: 17/435,974

(22) PCT Filed: Jun. 21, 2021

(86) PCT No.: PCT/JP2021/023417
§ 371 (c)(1),
(2) Date: Sep. 2, 2021

(87) PCT Pub. No.: WO2022/044509
PCT Pub. Date: Mar. 3, 2022

(65) Prior Publication Data
US 2022/0061754 A1     Mar. 3, 2022

(30) Foreign Application Priority Data

Aug. 31, 2020 (JP) .................................. 2020-145822

(51) Int. Cl.
*A61B 5/352* (2021.01)
*A61B 5/00* (2006.01)
(Continued)

(52) U.S. Cl.
CPC ............ *A61B 5/4842* (2013.01); *A61B 5/021* (2013.01); *A61B 5/0205* (2013.01);
(Continued)

(58) Field of Classification Search
None
See application file for complete search history.

(56) References Cited

U.S. PATENT DOCUMENTS

2019/0282178 A1    9/2019  Volosin et al.
2020/0297233 A1*   9/2020  Mitchell ................ A61B 5/316

FOREIGN PATENT DOCUMENTS

JP      2003-153864 A     5/2003
JP      2010-514497 A     5/2010
(Continued)

OTHER PUBLICATIONS

First Office Action in Japanese Applcation No. 2020-145822 dated Dec. 28, 2020 (8 pages).
(Continued)

*Primary Examiner* — Jon Eric C Morales
(74) *Attorney, Agent, or Firm* — Harness, Dickey & Pierce, P.L.C.

(57) ABSTRACT

An information processing system is provided to reduce labor of medical staff in determining heart failure stage. The information processing system is configured to execute: a reading step of reading out an input first electrocardiogram including an electrocardiogram of a user; and a determination step of determining a heart failure stage of the user based on the first electrocardiogram and reference information, wherein the reference information is information showing a relationship between the second electrocardiogram, including the electrocardiogram obtained beforehand, in which the heart failure stage has been determined by the physician, and a feature quantity of the heart failure,
(Continued)

wherein: the reference information is a learned model in which the feature quantity of the heart failure is learned from the second electrocardiogram, and the learned model is a model that learned a content determined in the determination step and corresponding clinical data.

12 Claims, 20 Drawing Sheets

(51) Int. Cl.
```
A61B 5/361      (2021.01)
A61B 5/0205     (2006.01)
G16H 10/60      (2018.01)
A61B 5/024      (2006.01)
A61B 5/271      (2021.01)
A61B 5/339      (2021.01)
A61B 5/021      (2006.01)
```
(52) U.S. Cl.
CPC .......... *A61B 5/02405* (2013.01); *A61B 5/271* (2021.01); *A61B 5/339* (2021.01); *A61B 5/352* (2021.01); *A61B 5/361* (2021.01); *A61B 5/6825* (2013.01); *G16H 10/60* (2018.01)

(56) References Cited

FOREIGN PATENT DOCUMENTS

| | | | |
|---|---|---|---|
| JP | 2011-062367 | A | 3/2011 |
| JP | 2012-504478 | A | 2/2012 |
| JP | 2014-507187 | A | 3/2014 |
| JP | 2015-231427 | A | 12/2015 |
| JP | 2018-524079 | A | 8/2018 |
| JP | 2018-173962 | A | 11/2018 |
| JP | 2020-039472 | A | 3/2020 |

OTHER PUBLICATIONS

Second Office Action in Japanese Applcation No. 2020-145822 dated Mar. 18, 2021 (8 pages).
Tripoliti Evanthia E et al: "Estimation of New York Heart Association class in heart failure patients based on machine learning techniques", 2017 IEEE EMBS International Conference on Biomedical & Health Informatics (BHI), IEEE, dated Feb. 16, 2017, pp. 421-424 (total 4 pages).
Suidi Gabriele et al: "A Machine Learning System to Improve Heart Failure Patient Assistance", IEEE Journal of Biomedical and Health Informatics, IEEE, Piscataway, NJ, USA; vol. 18, No. 6; dated Nov. 6, 2014; pp. 1750-1756 (total 7 pages).
Extended European Search Report issued for the corresponding European Patent Application No. 21773262.7; dated May 27, 2022 (total 12 pages).

\* cited by examiner

Fig. 5
SCALE
RISK OF HEART FAILURE
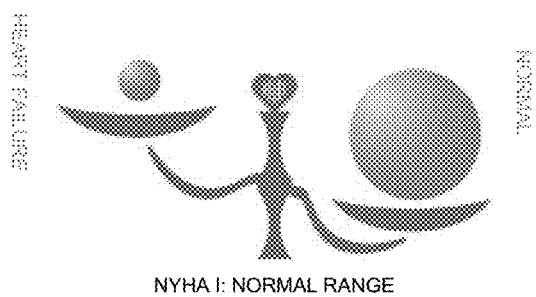
NYHA I: NORMAL RANGE
RISK OF HEART FAILURE
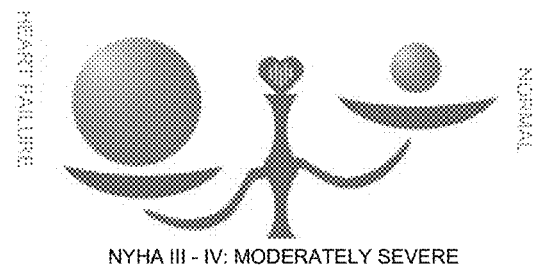
NYHA III - IV: MODERATELY SEVERE
Y HEART RATE, X HEART FAILURE LEVEL
CHANGE OF HEART FAILURE LEVEL
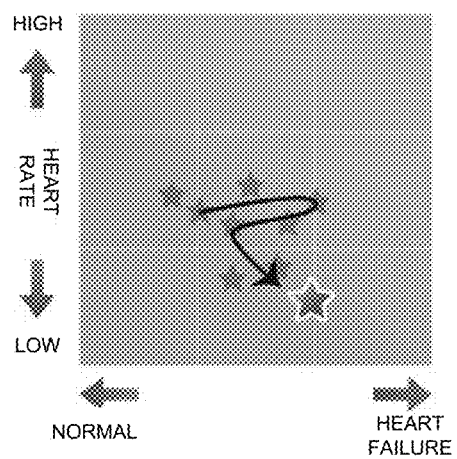
★ LATEST   ★ PAST
→ TRAJECTORY FOR PAST 3 TIMES Fig. 6
TACHOMETER
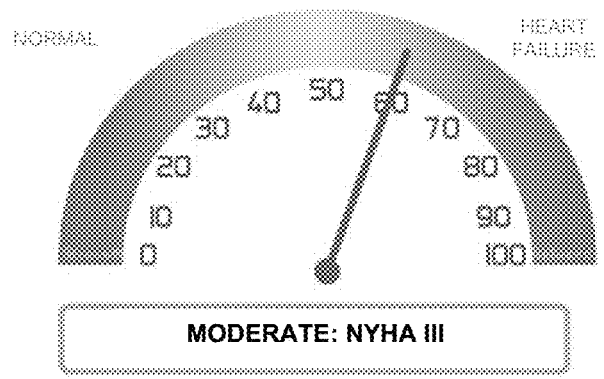
REPRESENT IN COLOR AND LETTER
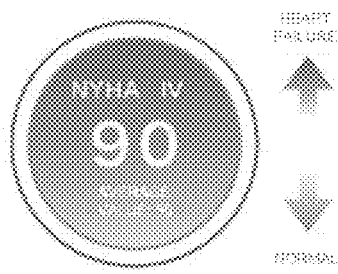
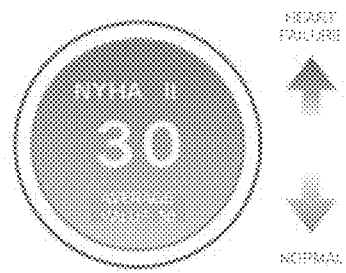
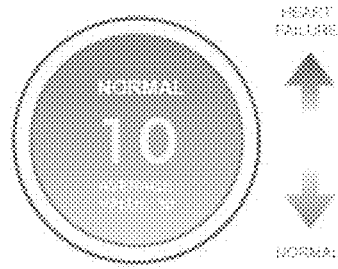

BAR DISPLAY

HEART FAILURE LEVEL

NORMAL RANGE

← HEART FAILURE          NORMAL →

BAR DISPLAY LIST

| 2018 9/2 9:00 DAY | HEART FAILURE LEVEL | NORMAL RANGE |
| 2018 9/21 10:00 DAY | HEART FAILURE LEVEL | MODERATELY SEVERE |
| 2018 9/21 13:00 DAY | HEART FAILURE LEVEL | NORMAL |
| 2018 9/21 18:00 DAY | HEART FAILURE LEVEL | MILD |

DISPLAY MEDIUM VALUE IN CENTER (1 DAY)

Fig. 9
DISPLAY IN ICON
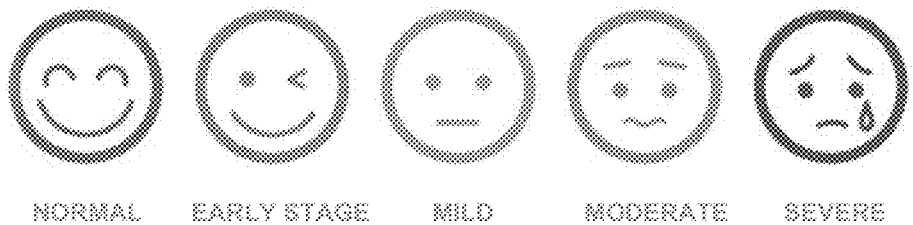
HEART FAILURE LEVEL
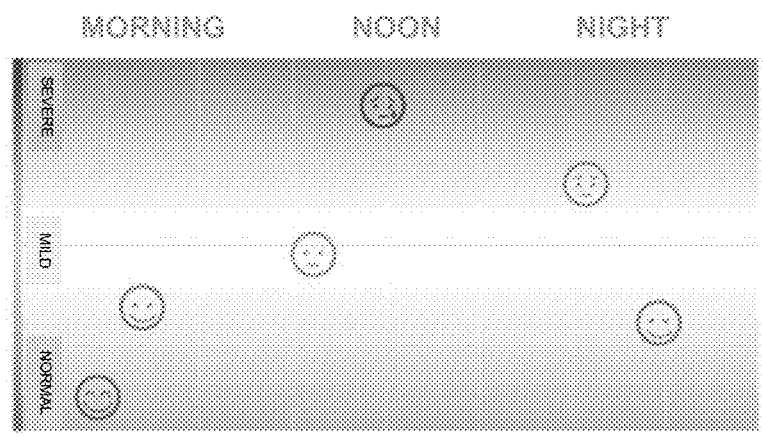
LEVEL METER
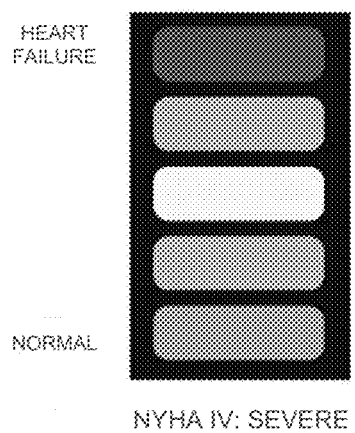
NYHA IV: SEVERE
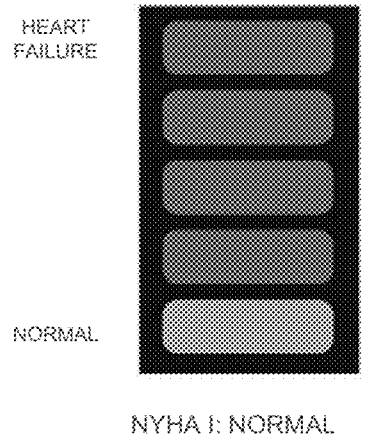
NYHA I: NORMAL Fig. 10
DISPLAY IN AREA
CHANGE OF HEART FAILURE LEVEL
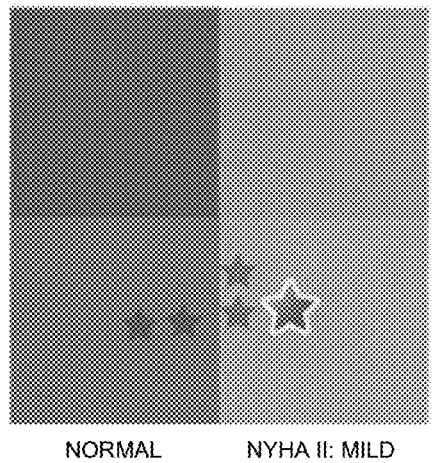
NYHA IV: SEVERE    NYHA III: MODERATE
NORMAL    NYHA II: MILD
★ LATEST    ☆ PAST
CHANGE OF HEART FAILURE LEVEL
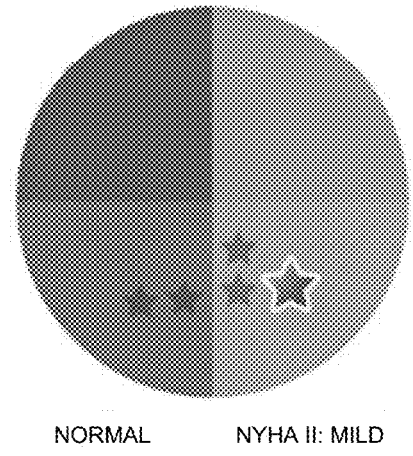
NYHA IV: SEVERE    NYHA III: MODERATE
NORMAL    NYHA II: MILD
★ LATEST    ☆ PAST Fig. 12
DISPLAY IN CANDLE
(NUMBER OF THINGS)
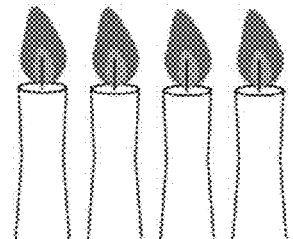
NORMAL
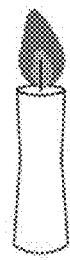
NYHA IV: SEVERE Fig. 13
DISPLAY IN CLUSTERING (CASE OF 3 CLASSIFICATIONS)
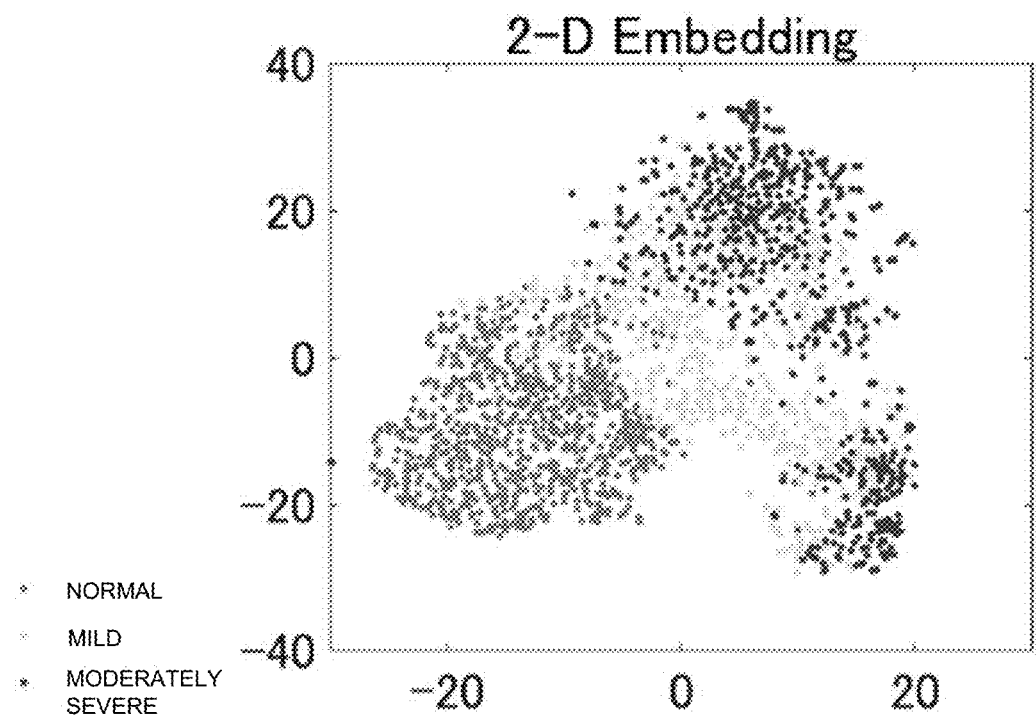
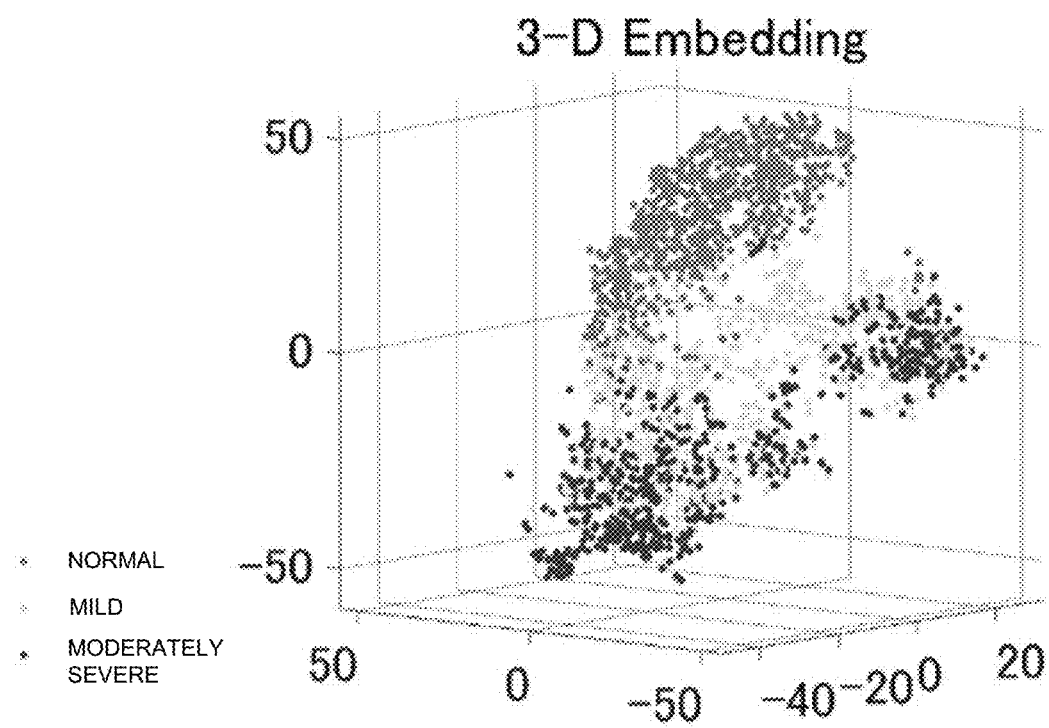

Fig. 14 DISPLAY IN CLUSTERING (CASE OF 4 CLASSIFICATIONS)
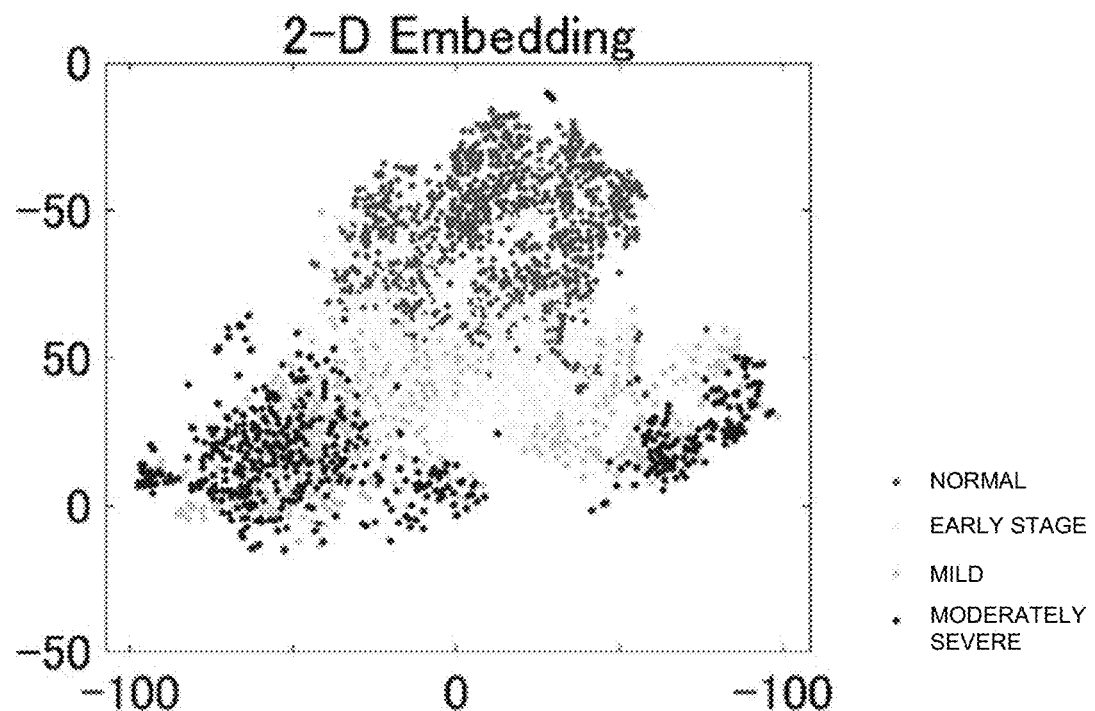
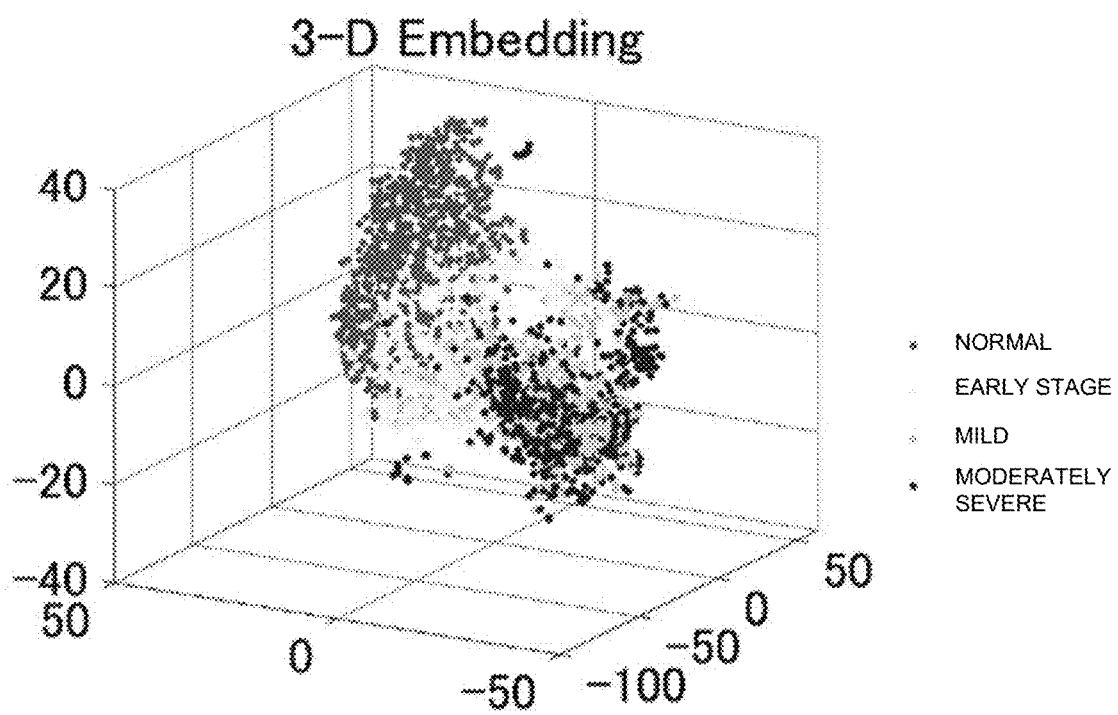

INFORMATION PROCESSING SYSTEM AND PROGRAM

CROSS REFERENCE TO RELATED APPLICATIONS

This application is a U.S. National Phase Application under 35 U.S.C. 371 of International Application No. PCT/JP2021/23417, filed on Jun. 21, 2021, which claims priority to Japanese Patent Application No. 2020-145822, filed on Aug. 31, 2020. The entire disclosures of the above applications are expressly incorporated by reference herein.

BACKGROUND

Technical Field

The present invention relates to an information processing system and a program.

Related Art

A method of detecting heart failure has been disclosed in which the electrocardiogram, heart rate, heart rate variability, heart rate interval, and respiratory frequency are obtained from the user, and information thereof is analyzed to determine whether or not the user has heart failure (see JP 2020-039472).

However, the technology disclosed in JP 2020-039472 does not determine the severity of the heart failure (heart failure stage). Further, since various information needed to be obtained from the user, it is time-consuming to determine the heart failure.

The present invention has been in view of the above circumstances and provides an information processing system capable of reducing labor of medical staff in determining the heart failure stage.

SUMMARY

According to one aspect of the present invention, an information processing system is provided. The information processing system is configured to execute: a reading step of reading out an input first electrocardiogram including an electrocardiogram of a user; and a determination step of determining a heart failure stage of the user based on the first electrocardiogram and reference information, wherein the reference information is information showing a relationship between the second electrocardiogram, including the electrocardiogram obtained beforehand, in which the heart failure stage has been determined by the physician, and a feature quantity of the heart failure, wherein: the reference information is a learned model in which the feature quantity of the heart failure is learned from the second electrocardiogram, and the learned model is a model that learned a content determined in the determination step and corresponding clinical data.

According to the above disclosure, it is possible to provide an information processing system capable of reducing labor of medical staff in determining the heart failure stage.

BRIEF DESCRIPTION OF THE DRAWINGS

FIG. 5 is a diagram showing a representation method of a determination result of the heart failure stage.

FIG. 6 is a diagram showing a representation method of a determination result of the heart failure stage.

FIG. 9 is a diagram showing a representation method of a determination result of the heart failure stage.

FIG. 10 is a diagram showing a representation method of a determination result of the heart failure stage.

FIG. 12 is a diagram showing a representation method of a determination result of the heart failure stage.

FIG. 13 is a diagram showing a representation method of a determination result of the heart failure stage.

FIG. 14 is a diagram showing a representation method of a determination result of the heart failure stage.

DETAILED DESCRIPTION

Hereinafter, embodiments of the present invention will be described with reference to the drawings. Various features described in the embodiment below can be combined with each other.

A program for realizing a software in the present embodiment may be provided as a non-transitory computer readable medium that can be read by a computer, or may be provided for download from an external server, or may be provided so that the program can be activated on an external computer to realize its functions on a client terminal (so-called cloud computing).

In the present embodiment, the "unit" may include, for instance, a combination of hardware resources implemented by circuits in a broad sense and information processing of software that can be concretely realized by these hardware resources. Further, although various information is performed in the present embodiment, this information can be represented, for example, by physical signal values representing voltage and current, by high and low signal values as a bit set of binary numbers composed of 0 or 1, or by quantum superposition (so-called quantum bits). In this way, communication/calculation can be performed on a circuit in a broad sense.

Further, the circuit in a broad sense is a circuit realized by combining at least an appropriate number of a circuit, a circuitry, a processor, a memory, and the like. In other words, it is a circuit includes Application Specific Integrated Circuit (ASIC), Programmable Logic Device (e.g., Simple Programmable Logic Device (SPLD), Complex Programmable Logic Device (CPLD), and Field Programmable Gate Array (FPGA)), and the like.

First Embodiment

The first embodiment will be described as follows.
1. Configuration of an Information Processing System 100

Figure 1:
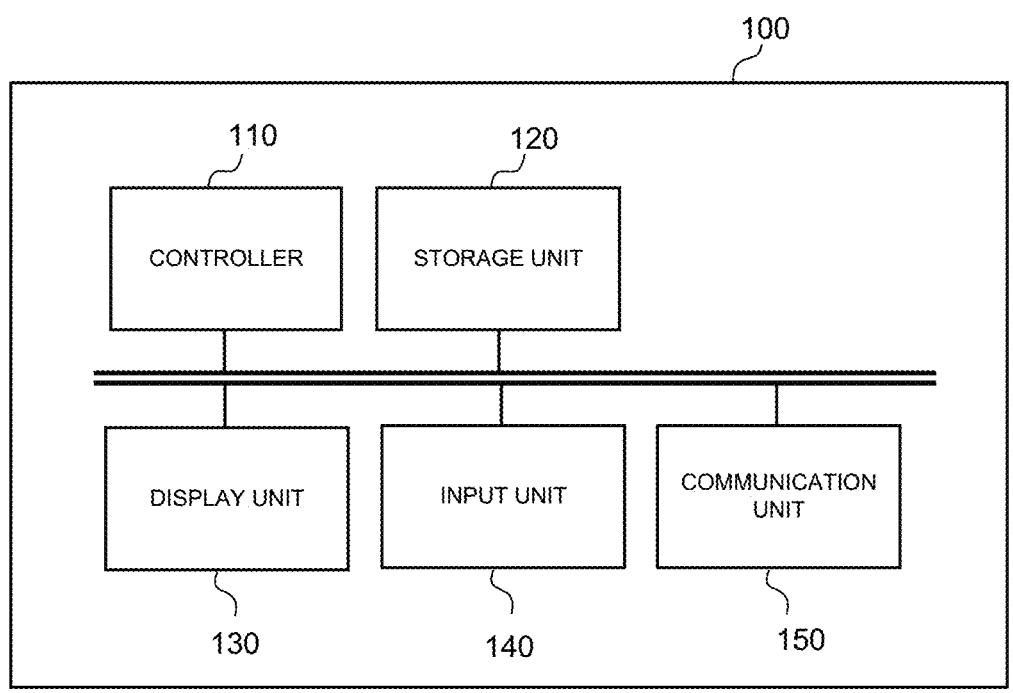
FIG. 1 is a block diagram showing a configuration of an information processing system 100.

FIG. 1 is a block diagram showing a configuration of an information processing system 100. As shown in FIG. 1, the information processing system 100 has a controller 110, a storage unit 120, a display unit 130, an input unit 140, and a communication unit 150. The controller 110 is a CPU (Central Processing Unit), GPU (Graphics Processing Unit), or the like, and controls the entire information processing system 100. The storage unit 120 stores various programs and data, and is configured of, for example, memory, HDD (Hard Disk Drive), ROM (Read Only Memory), RAM (Random Access Memory), and the like.

The storage unit 120 stores data or the like used when the controller 110 executes processing based on the program. By executing processing by the controller 110 based on the program stored in the storage unit 120, various processing described below are realized. In other words, the program causes the computer to execute each step of the information processing system 100. As for the storage unit 120, at least a part of the information may be stored in an external server other than the storage unit 120, or may be stored in a plurality of terminals in a distributed manner using blockchain technology or the like.

The display unit 130 displays text or images (including still and moving images) and is configured with any display. The input unit 140 inputs various information to the information processing system 100, and is configured of mouse, keyboard, pointing device, and the like. The communication unit 150 is a NIC (Network Interface Card) or the like, and connects the information processing system 100 to a network, and is configured to enable data communication with other device or component through wired or wireless connection.
2. Functional Configuration of the Information Processing System 100

Figure 2:
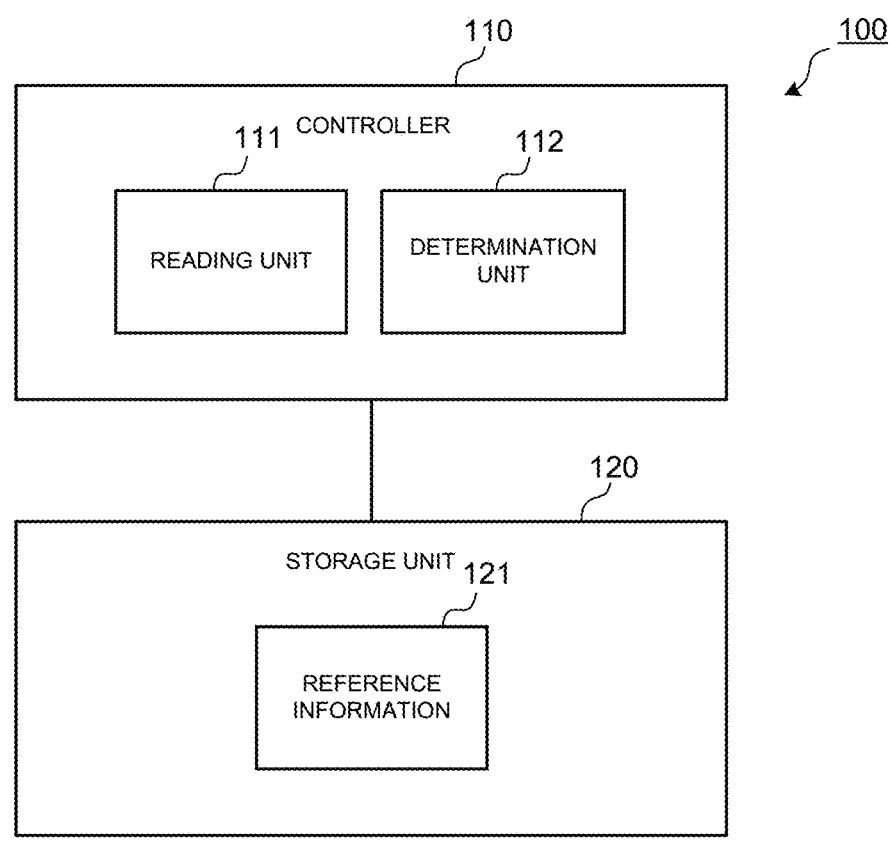
FIG. 2 is a block diagram showing a functional structure of the information processing system 100.

FIG. 2 is a block diagram showing a functional structure of the information processing system 100. As shown in FIG. 2, the controller 110 comprises a reading unit 111 and a determination unit 112. The reading unit 111 is a unit in which information processing by a software (stored in the storage unit 120) is specifically realized by a hardware (the controller 110). The reading unit 111 is configured to execute the reading step. The reading unit 111 reads out the input first electrocardiogram. The first electrocardiogram indicates the electrocardiogram obtained from the user. Reading out the first electrocardiogram means, for example, receiving the first electrocardiogram from an external device via the communication unit 150, writing to the storage unit 120 (e.g., RAM) by reading out the first electrocardiogram, reading out the first electrocardiogram stored in the storage unit 120 (e.g., HDD) beforehand in response to an operation of the input unit 140 by the user, and writing to the storage unit 120 (e.g., RAM), or writing the first electrocardiogram transmitted from a predetermined electrocardiogram measurement terminal to a cloud and stored in a storage apparatus (e.g., HDD) of a server to a storage apparatus (e.g., RAM) of a server by a control apparatus (e.g., CPU) of the server, or the like. Of course, these are only examples and are not limited to these.

The determination unit 112 is a unit in which information processing by the software (stored in the storage unit 120) is specifically realized by the hardware (the controller 110). The determination unit 112 is configured to perform a determination step. The determination unit 112 determines the heart failure stage based on the first electrocardiogram and the reference information 121. The reference information 121 is stored in the storage unit 120 (e.g., ROM). Here, the reference information 121 is information that indicates the relationship between the second electrocardiogram and a feature quantity of the heart failure. Examples of the reference information include look-up table, function, mathematical model, learned model, or the like. Of course, these are only examples and are not limited to these. The heart failure stage refers to a four-stage classification of heart failure severity based on the degree of subjective symptoms caused by physical activity, created by NYHA (New York Heart Association). Moreover, the second electrocardiogram indicates the electrocardiogram that has been obtained in advance and for which the heart failure stage has been determined by a physician.

Figure 3:
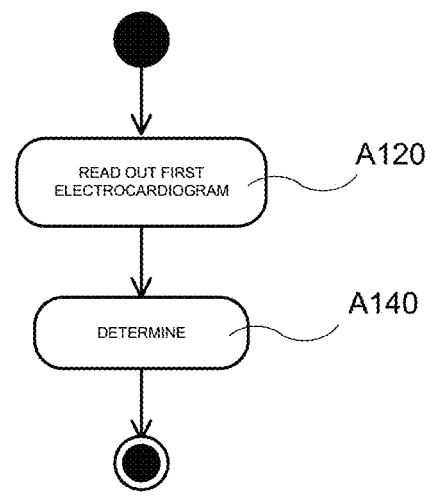
FIG. 3 is an activity diagram showing information processing of a controller 110.

Here, to determine means, for example, that a look-up table is stored in the storage unit 120 (e.g., ROM or HDD) in advance and the controller 110 reads out the look-up table from the storage unit 120 to determine, that a function is stored in the storage unit 120 (e.g., ROM or HDD) in advance and the decision is made by inputting the feature quantity obtained from the first electrocardiogram to the function, that a mathematical model is stored in the storage unit 120 (e.g., ROM or HDD) in advance and the decision is made by inputting the feature quantity obtained from the first electrocardiogram to the mathematical model, or the decision is made by inputting the feature quantity obtained from the first electrocardiogram to the learned model based on the learned model that learned the second electrocardiogram and the feature quantity of the heart failure. Of course, these are only examples and are not limited to these.
3. Information Processing FIG. 3 is an activity diagram showing information processing of the controller 110. As shown in FIG. 3, the reading unit 111 reads out the input first electrocardiogram (A120). Next, the determination unit 112 determines the heart failure stage based on the first electrocardiogram and the reference information (A140).

FIGS. 4A to 4D are diagrams showing determination results of the heart failure stage. Specifically, in FIGS. 4A to 4D, first electrocardiograms 311, 321, 331, 341 are read out by the reading unit 111, and the determination results 312, 322, 332, 342 of the heart failure stage determined by the determination unit 112 are displayed based on the read out first electrocardiograms 311, 321, 331, 341 and the reference information.

Figure 4A:
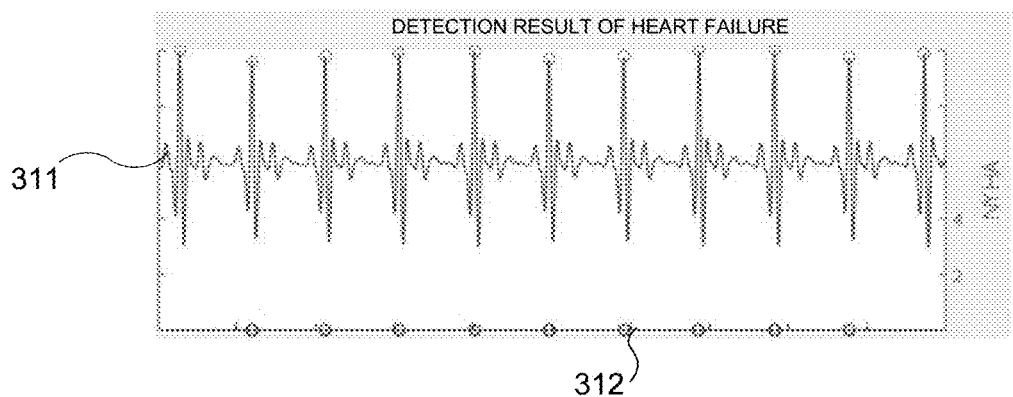
FIG. 4A is a diagram showing the normalized electrocardiogram and heart failure stage of a healthy person.
Figure 4B:
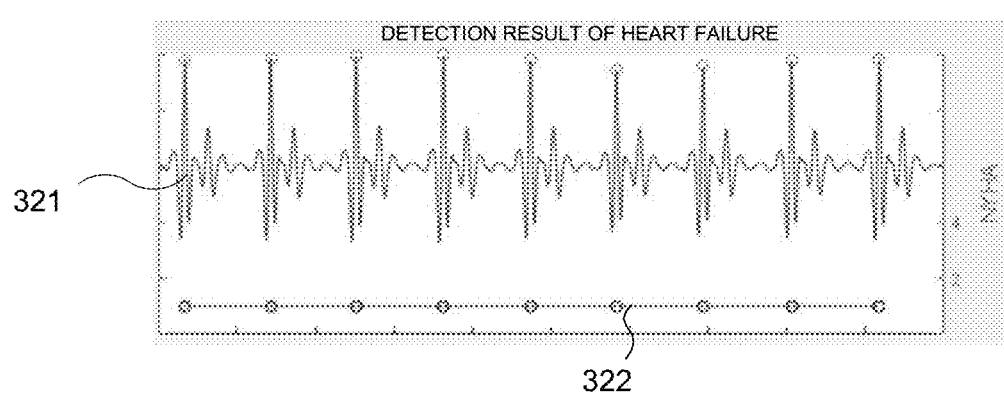
FIG. 4B is a diagram showing the normalized electrocardiogram and heart failure stage at early stage.
Figure 4C:
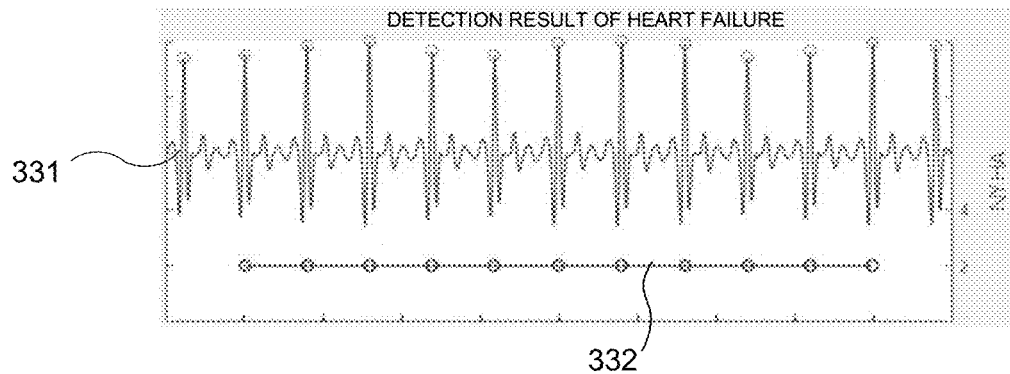
FIG. 4C is a diagram showing the normalized electrocardiogram and heart failure stage in mild.
Figure 4D:
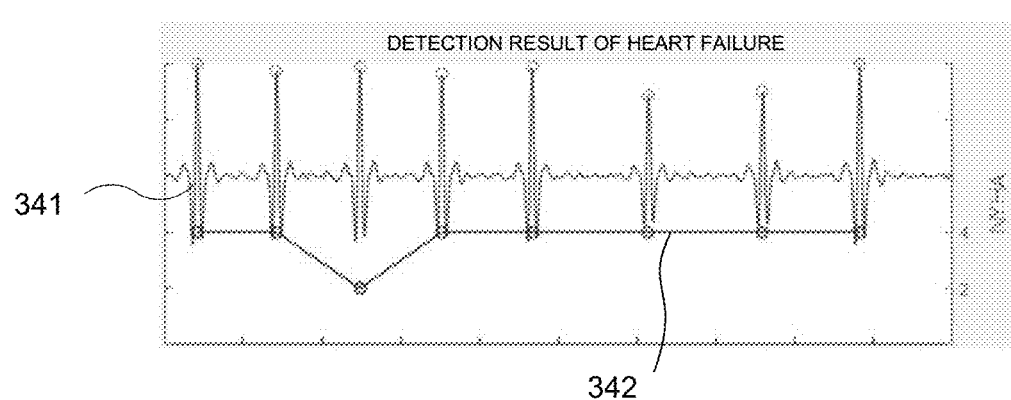
FIG. 4D is a diagram showing the normalized electrocardiogram and heart failure stage in moderately severe.
Figure 7:
FIG. 7 is a diagram showing a representation method of a determination result of the heart failure stage.
Figure 8:
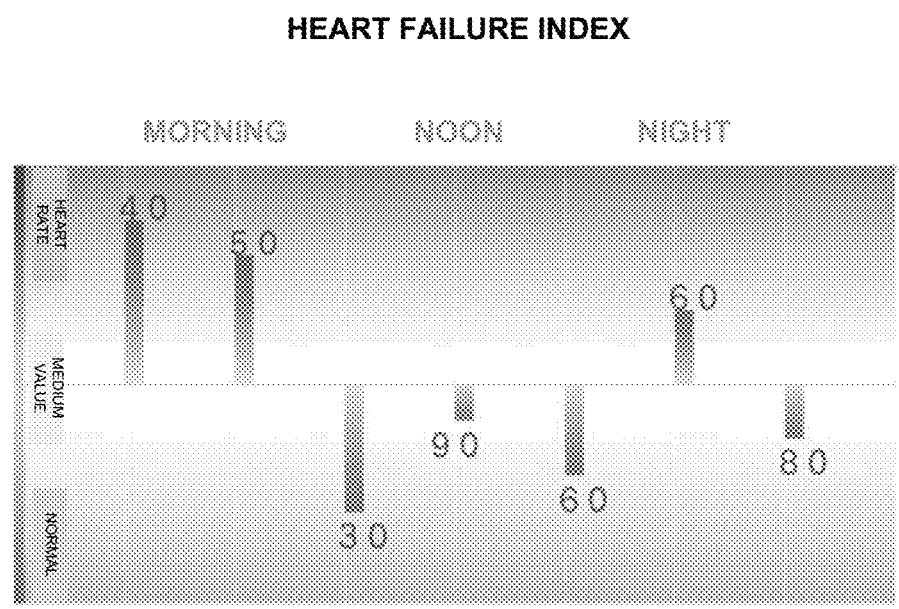
FIG. 8 is a diagram showing a representation method of a determination result of the heart failure stage.
Figure 11:
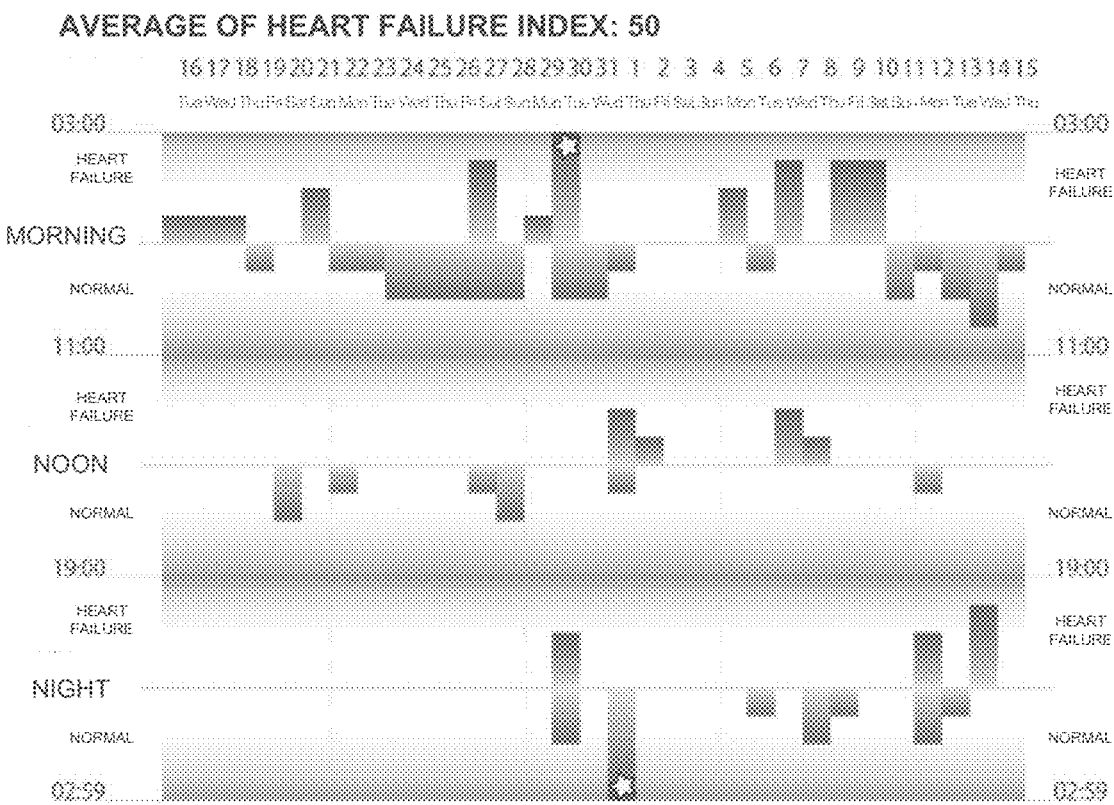
FIG. 11 is a diagram showing a representation method of a determination result of the heart failure stage.

As shown in FIG. 4A, the NYHA corresponding to the determination result 312 shows 0 in all 9 heartbeats, which indicates a case of a healthy person. As shown in FIG. 4B, the NYHA corresponding to the determination result 322 shows 1 in all 9 heartbeats, which indicates a case where the heart failure stage is early. As shown in FIG. 4C, the NYHA corresponding to the determination result 332 shows 2 in all 11 heartbeats, which indicates a case where the heart failure stage is mild. As shown in FIG. 4D, the NYHA corresponding to the determination result 342 shows 2 for the third heartbeat out of 8 heartbeats, but 4 for the other 7 heartbeats, and since 4 is dominant, this indicates a case where the heart failure stage is moderately severe.

Various screen examples displayed on the display unit 130 of the information processing system 100 or a second user terminal 220 described below are shown in FIGS. 5 to 14 for reference. According to the screen examples shown in FIGS. 5 to 14, the user can easily grasp the determination results of the heart failure stage.

In summary, the information processing method is configured to execute the reading step and the determination step.

The reading step reads out the input first electrocardiogram. The determination step determines the heart failure stage based on the first electrocardiogram and the reference information. The reference information is information indicating a relationship between the second electrocardiogram and the feature quantity of the heart failure.

In the first embodiment, if the input first electrocardiogram exists, the heart failure stage can be automatically determined. That is, since there is no need to obtain various information from the user, the labor of medical staff in determining the heart failure stage can be reduced.

Second Embodiment

The second embodiment will be illustrated hereinafter. In the second embodiment, the description of the parts that overlap with the first embodiment will be appropriately omitted.

The first electrocardiogram is preferably configured of 1 to 50 beats. Specifically, for example, it is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 beats, and may be in a range between any two of the numerical values illustrated above. In particular, it is preferably one beat. The determination unit 112 determines the heart failure stage based on the first electrocardiogram configured of 1 to 50 beats and the reference information.

The first electrocardiogram is preferably configured of heartbeats of 5 to 300 seconds. Specifically, for example, it is 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 seconds, and may be in the range between any two of the numerical values illustrated above. In particular, it is preferably 5 seconds. The determination unit 112 determines the heart failure stage based on the first electrocardiogram configured of heartbeats of 5 to 300 seconds and the reference information.

In the second embodiment, the heart failure stage can be automatically determined if the first electrocardiogram indicating 1 to 50 beats and heartbeats of 5 to 300 seconds exists. Therefore, the time to obtain the first electrocardiogram can be reduced, and the heart failure stage can be determined quickly.

Third Embodiment

The third embodiment will be illustrated hereinafter. In the third embodiment, the description of the parts that overlap with the first and second embodiments will be appropriately omitted.

The first electrocardiogram is preferably configured of one lead. The determination unit 112 determines the heart failure stage based on the first electrocardiogram configured of the one lead and the reference information. The first electrocardiogram is usually configured of 6 types of limb leads and 6 types of chest leads, and the one lead indicates any one of these leads.

In the third embodiment, the heart failure stage can be automatically determined if the first electrocardiogram regarding the one lead exists. That is, since the labor for attaching electrodes to the user can be eliminated, the labor of medical staff can be reduced.

Fourth Embodiment

The fourth embodiment will be illustrated hereinafter. In the fourth embodiment, the description of the parts that overlap with the first, second and third embodiments will be appropriately omitted.

Figure 15:
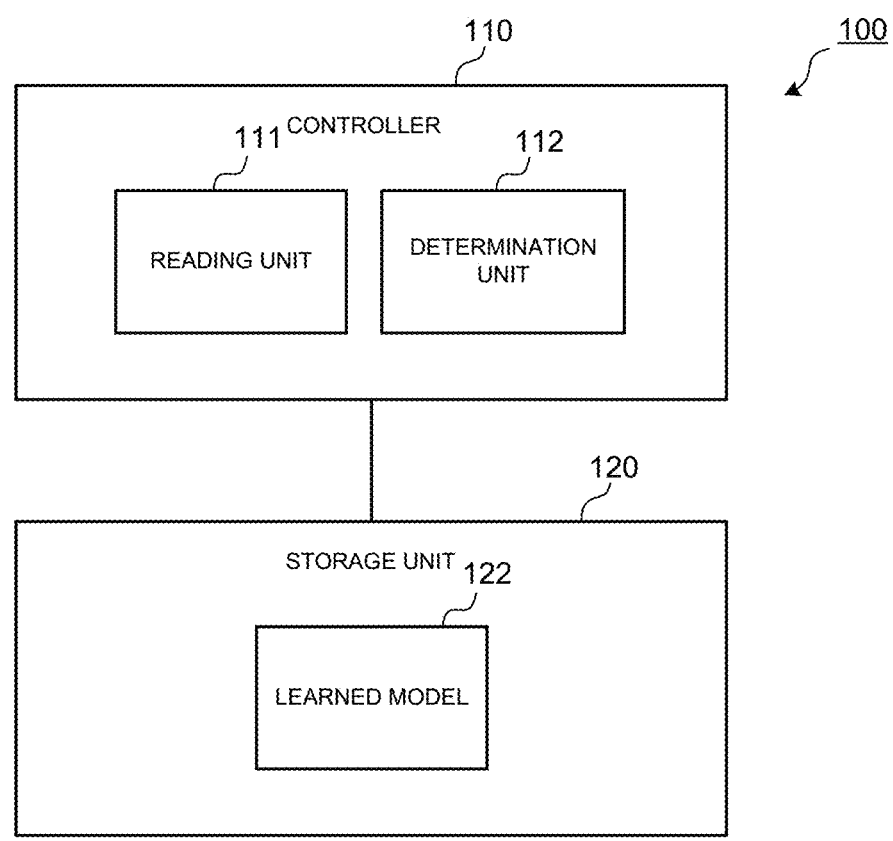
FIG. 15 is a block diagram showing the functional structure of the information processing system 100.

FIG. 15 is a block diagram showing the functional structure of the information processing system 100. As shown in FIG. 15, it is preferable that the reference information stored in the storage unit 120 is a learned model 122 in which the feature quantity of heart failure is learned from the second electrocardiogram. The learned model 122 is, for example, a learned model in which the feature quantity of heart failure is learned from the second electrocardiogram by deep learning or machine learning such as CNN (Convolutional Neural Network).

Figure 16A:
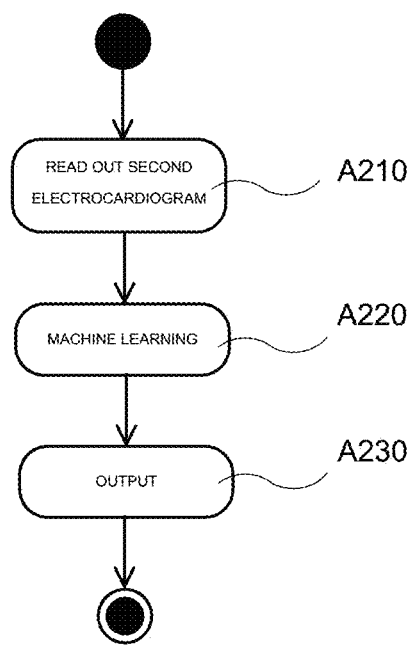
FIG. 16A is an activity diagram showing a generation method of a learned model 122.

FIG. 16A is an activity diagram showing a generation method of the learned model 122. Here, machine learning will be illustrated as an example. As shown in FIG. 16A, the controller 110 (e.g., CPU) reads out the second electrocardiogram stored in the storage unit 120 (e.g., HDD) (A210). Next, the controller 110 (e.g., GPU) performs machine learning regarding the second electrocardiogram (A220). Then, the controller 110 (e.g., GPU) performs the output processing (A230). Here, the learned model 122 is generated by repeatedly performing A210 to A230.

Here, the learned model is a model that learned a content determined in the determination unit 112 and corresponding clinical data. The clinical data is data including at least one of age, gender, BMI (Body Mass Index), PWTT (Pulse Wave Transit Time), blood pressure, heart rate, SDNN (Standard Deviation of The NN Interval), CVRR (Coefficient of Variation of RR Interval), atrial fibrillation, or HRV (Heart Rate Variability).

Figure 16B:
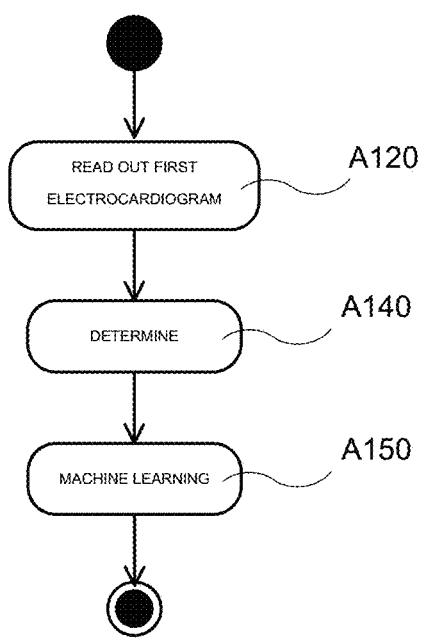
FIG. 16B is an activity diagram showing information processing of a controller 110.

FIG. 16B is an activity diagram showing information processing of the controller 110. As shown in FIG. 16B, the reading unit 111 reads out the input first electrocardiogram (A120). Next, the determination unit 112 determines the heart failure stage based on the first electrocardiogram and the reference information (A140). Then, the controller 110 causes the learned model 122 to machine learn the content determined in A140 and corresponding clinical data (A150).

In the fourth embodiment, by using the learned model 122 as reference information, the heart failure stage can be determined with a high degree of accuracy by further learning the content determined in the determination unit 112 and corresponding clinical data.

Fifth Embodiment

The fifth embodiment will be illustrated hereinafter. In the fifth embodiment, the description of the parts that overlap with the first, second, third and fourth embodiments will be appropriately omitted.

Figure 17:
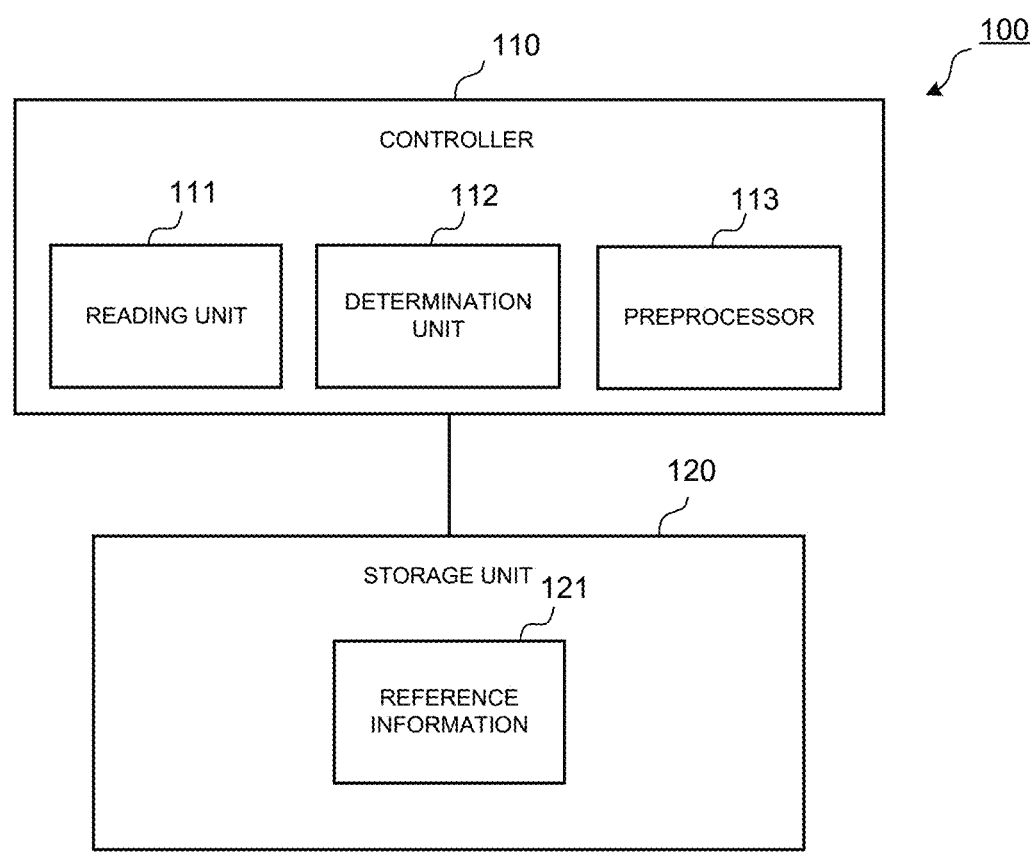
FIG. 17 is a block diagram showing the functional structure of the information processing system 100.

FIG. 17 is a block diagram showing the functional structure of the information processing system 100. As shown in FIG. 17, the controller 110 is preferably further comprises a preprocessor 113. The preprocessor 113 is specifically realized by hardware (the controller 110) with information processing by software (stored in the storage unit 120). The preprocessor 113 is configured to execute a preprocessing step. The preprocessor 113 preprocesses the first electrocardiogram read out by the reading unit 111. Here, to preprocess indicates, for example, that a predetermined parameter necessary for removing noise in the first electrocardiogram are stored in the storage unit 120 (e.g., ROM or HDD) in advance, and that the controller 110 reads out the first electrocardiogram and the predetermined parameter from the storage unit 120 and performs processing. The preprocessing may include, for example, trend removal, motion artifact removal, noise removal, waveform cutout for each heartbeat, and normalization. These may be combined with each other for preprocessing.

Figure 18:
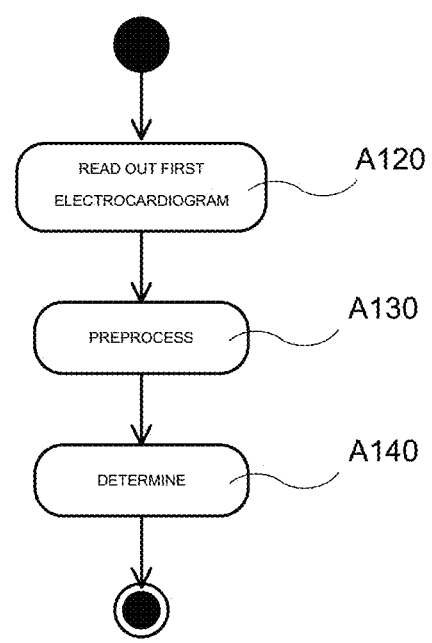
FIG. 18 is an activity diagram showing the information processing of the controller 110.

FIG. 18 is an activity diagram showing the information processing of the controller 110. As shown in FIG. 18, the reading unit 111 reads out the input first electrocardiogram (A120). Next, the preprocessor 113 preprocesses the first electrocardiogram (A130). Then, the determination unit 112 determines the heart failure stage based on the preprocessed first electrocardiogram and the reference information (A140).

In the fifth embodiment, the heart failure stage can be determined with a high degree of accuracy by preprocessing the first electrocardiogram to make it easier to determine the heart failure stage.

Sixth Embodiment

The sixth embodiment will be illustrated hereinafter. In the sixth embodiment, the description of the parts that overlap with the first, second, third, fourth, and fifth embodiments will be appropriately omitted.

The one lead is preferably a lead I. Here, the lead I is obtained from a right hand and a left hand of the user and giving a view of the lateral wall of the left ventricle in the heart.

In the sixth embodiment, the heart failure stage can be automatically determined if the first electrocardiogram for the lead I exists. In other words, since the electrodes are attached only to the right hand and the left hand of the user, the labor for attaching electrodes to the user can be eliminated, thus the labor of medical staff can be reduced.

Seventh Embodiment

The seventh embodiment will be illustrated hereinafter. In the seventh embodiment, the description of the parts that overlap with the first, second, third, fourth, fifth and sixth embodiments will be appropriately omitted.

Figure 19:
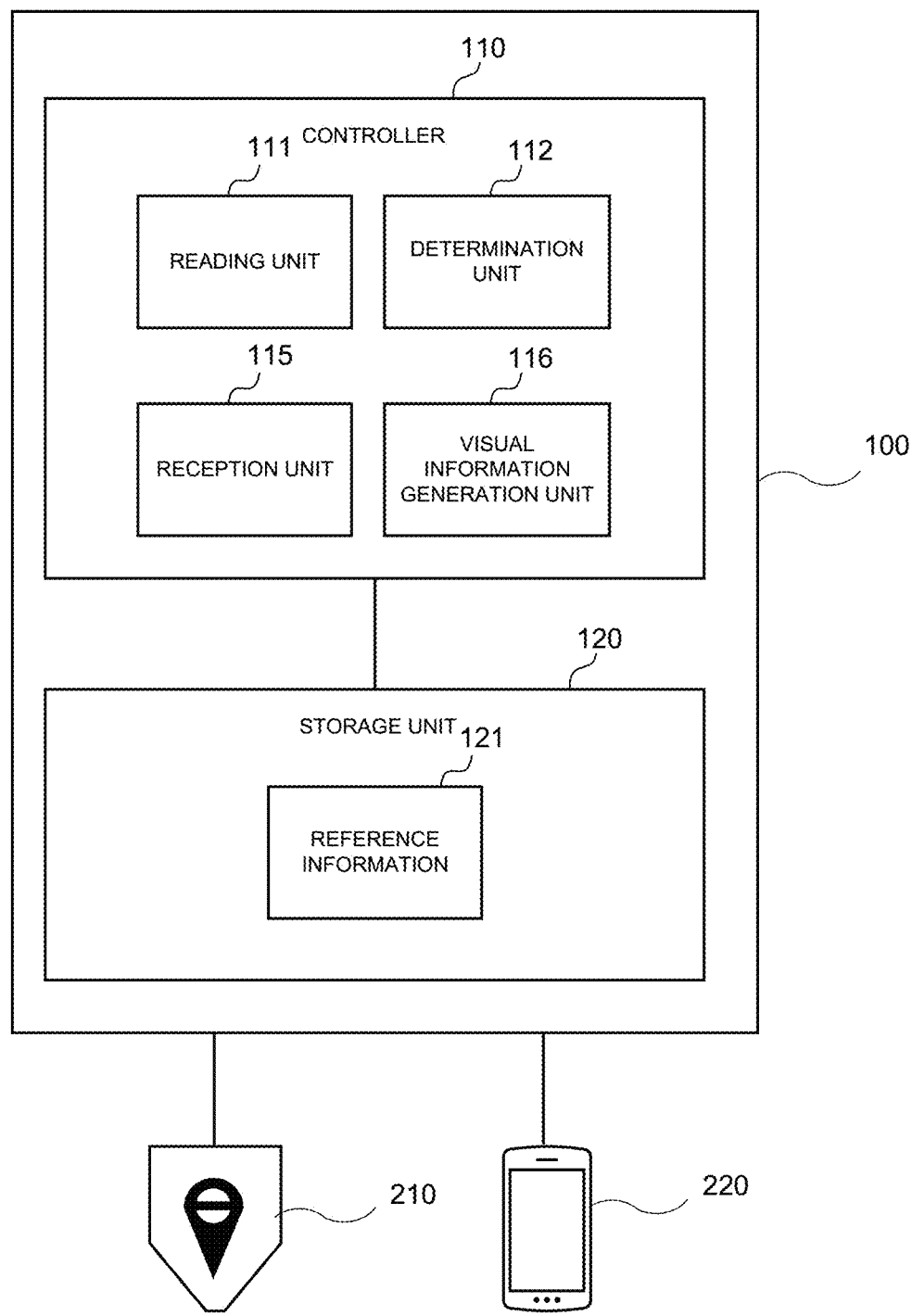
FIG. 19 is a block diagram showing the functional structure of the information processing system 100.

FIG. 19 is a block diagram showing the functional structure of the information processing system 100. As shown in FIG. 19, the controller 110 is preferably further comprises a reception unit 115 and a visual information generation unit 116. The reception unit 115 is specifically realized by hardware (the controller 110) with information processing by software (stored in the storage unit 120). The reception unit 115 is configured to execute a reception step. The reception unit 115 receives the first electrocardiogram from a first user terminal 210. The first user terminal 210 is, for example, a simple electrocardiograph, a wearable terminal, a 12-lead electrocardiograph, a bedside monitor, or a Holter electrocardiograph. Here, to receive indicates, for example, receiving the first electrocardiogram obtained in the first user terminal 210 via the communication unit 150.

The visual information generation unit 116 is specifically realized by hardware (the controller 110) with information processing by software (stored in the storage unit 120). The visual information generation unit 116 is configured to execute a visual information generation step. The visual information generation unit 116 generates visual information that can be seen by the second user terminal 220 from a result of the determination unit 112. The second user terminal 220 may be, for example, a computer, a smart phone, or a tablet. Here, to generate the visual information indicates, for example, generating visual information such as screen, image, rendering information, or the like when displaying the results of the heart failure stage determination stored in the storage unit 120 (e.g., RAM or HDD) on the second user terminal 220. The first user terminal 210 and the second user terminal 220 may be the same terminal.

Figure 20:
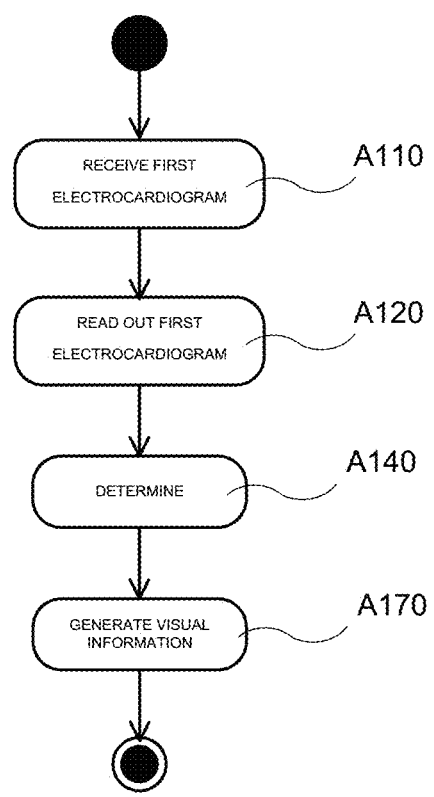
FIG. 20 is an activity diagram showing the information processing of the controller 110.

FIG. 20 is an activity diagram showing the information processing of the controller 110. As shown in FIG. 20, the reception unit 115 receives the first electrocardiogram from the first user terminal 210 (A110). Next, the reading unit 111 reads out the input first electrocardiogram (A120). Then, the determination unit 112 determines the heart failure stage based on the first electrocardiogram and the reference information (A140). Next, the visual information generation unit 116 generates visual information that can be seen by the second user terminal 220 from the result determined in A140 (A170).

In the seventh embodiment, the user can confirm the heart failure stage on his or her own second user terminal 220, thus the user can pay attention to his or her own physical condition without being constrained by time or place. In other words, it is possible to raise awareness of heart failure to the user.

It may be provided in each of the following aspects.

In the information processing system, the clinical data is data including at least one of age, gender, BMI (Body Mass Index), PWTT (Pulse Wave Transit Time), blood pressure, heart rate, SDNN (Standard Deviation of The NN Interval), CVRR (Coefficient of Variation of RR Interval), atrial fibrillation, or HRV (Heart Rate Variability).

In the information processing system, the first electrocardiogram is configured of one lead.

In the information processing system, the one lead is a lead I, obtained from a right hand and a left hand of a user.

In the information processing system, a preprocessing step of preprocessing the first electrocardiogram read out in the reading step, wherein the preprocessing is a processing for removing noise in the first electrocardiogram.

In the information processing system, the first electrocardiogram is configured of 1 to 50 beats. In the information processing system, a reception step of accepting the first electrocardiogram from a first user terminal, and a visual information generation step of generating visual information that can be seen by a second user terminal from a result of the determination step.

A program, wherein: the program allows a computer to execute each step of the information processing system.

Of course, the above embodiments are not limited thereto.

What is claimed is:

1. An information processing system comprising:
an input interface configured to accept a user electrocardiogram of a user from a first user terminal;
a memory configured to store a program and a database, the database including a learned model in which a feature quantity of a heart failure is learned from a plurality of determined electrocardiograms of a plurality of persons via deep learning or machine learning, the plurality of determined electrocardiograms being obtained beforehand and including electrocardiograms in which a stage of the heart failure has been determined; and a processor configured to execute the program so as to:
  obtain the user electrocardiogram via the input interface;
  determine the stage of the heart failure of the user based on the user electrocardiogram and the learned model to generate a determination result; and
  perform the deep learning or the machine learning with respect to the learned model based on the determination result and corresponding clinical data,
wherein the processor is further configured to generate visual information based on the determination result, and the visual information is configured to be displaced at a second user terminal.

2. The information processing system according to claim 1,
wherein the clinical data includes at least one of age, gender, BMI (Body Mass Index), PWTT (Pulse Wave Transit Time), blood pressure, heart rate, SDNN (Standard Deviation of The NN Interval), CVRR (Coefficient of Variation of RR Interval), atrial fibrillation, or HRV (Heart Rate Variability).

3. The information processing system according to claim 1,
wherein the user electrocardiogram is configured by one lead.

4. The information processing system according to claim 3,
wherein the one lead is obtained from a right hand and a left hand of the user.

5. The information processing system according to claim 1,
wherein the processor is further configured to preprocess the user electrocardiogram to remove noise before the processor determines the stage of the heart failure of the user.

6. The information processing system according to claim 1,
wherein the user electrocardiogram corresponds to 1 to 50 beats.

7. A non-transitory computer-readable storage medium having computer-readable instructions for causing a computer to execute a process by a processor so as to perform the steps of:

obtaining a user electrocardiogram of a user from a first user terminal via an input interface;

reading a database from a memory, the database including a learned model in which a feature quantity of a heart failure is leaned from a plurality of determined electrocardiograms of a plurality of persons via deep learning or machine learning, the plurality of determined electrocardiograms being obtained beforehand and including electrocardiograms in which a stage of the heart failure has been determined;

determining the stage of the heart failure of the user based on the user electrocardiogram and the learned model to generate a determination result;

performing the deep learning or the machine learning with respect to the learned model based on the determination result and corresponding clinical data; and generating visual information based on the determination result, the visual information being configured to be displayed at a second user terminal.

8. The non-transitory computer-readable storage medium according to claim 7,
wherein the clinical data includes at least one of age, gender, BMI (Body Mass Index), PWTT (Pulse Wave Transit Time), blood pressure, heart rate, SDNN (Standard Deviation of The NN Interval), CVRR (Coefficient of Variation of RR Interval), atrial fibrillation, or HRV (Heart Rate Variability).

9. The non-transitory computer-readable storage medium according to claim 7,
wherein the user electrocardiogram is configured by one lead.

10. The non-transitory computer-readable storage medium according to claim 9,
wherein the one lead is obtained from a right hand and a left hand of the user.

11. The non-transitory computer-readable storage medium according to claim 7,
wherein the processor is further configured to preprocess the user electrocardiogram to remove noise before the processor determines the stage of the heart failure of the user.

12. The non-transitory computer-readable storage medium according to claim 7,
wherein the user electrocardiogram corresponds to 1 to 50 beats.

* * * * *